(12) United States Patent
Zhang et al.

(10) Patent No.: US 10,238,702 B2
(45) Date of Patent: Mar. 26, 2019

(54) PHARMACEUTICAL COMPOSITION, PREPARATION METHOD THEREFOR AND USE THEREOF

(71) Applicant: SICHUAN JIUZHANG BIOLOGICAL SCIENCE AND TECHNOLOGY CO., LTD, Chengdu, Sichuan (CN)

(72) Inventors: Jie Zhang, Sichuan (CN); Huarong Yang, Sichuan (CN); Chenxu Tian, Sichuan (CN); Lina Zhu, Sichuan (CN); Wang Huang, Sichuan (CN); Yongjiang Yan, Sichuan (CN)

(73) Assignee: SICHUAN JIUZHANG BIOLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 46 days.

(21) Appl. No.: 14/910,972

(22) PCT Filed: Aug. 21, 2013

(86) PCT No.: PCT/CN2013/081970
§ 371 (c)(1),
(2) Date: Feb. 8, 2016

(87) PCT Pub. No.: WO2015/024218
PCT Pub. Date: Feb. 26, 2015

(65) Prior Publication Data
US 2016/0184373 A1 Jun. 30, 2016

(51) Int. Cl.
| | | |
|---|---|---|
| A61K 9/00 | (2006.01) | |
| A61K 36/46 | (2006.01) | |
| A61K 47/69 | (2017.01) | |
| A61K 31/216 | (2006.01) | |
| A61K 36/074 | (2006.01) | |

(52) U.S. Cl.
CPC .......... *A61K 36/074* (2013.01); *A61K 9/0056* (2013.01); *A61K 31/216* (2013.01); *A61K 36/46* (2013.01); *A61K 47/6951* (2017.08)

(58) Field of Classification Search
CPC .............. A61K 2300/00; A61K 31/216; A61K 36/074; A61K 36/46; A61K 47/48969; A61K 47/6951; A61K 9/0056
See application file for complete search history.

(56) References Cited

U.S. PATENT DOCUMENTS

| | | | | |
|---|---|---|---|---|
| 2008/0112966 A1* | 5/2008 | Gow | ................... | A61K 36/074 424/195.15 |
| 2009/0169653 A1* | 7/2009 | Lin | ........................ | A61K 31/00 424/728 |
| 2012/0034323 A1* | 2/2012 | Doherty | ............... | A61K 36/258 424/727 |

FOREIGN PATENT DOCUMENTS

| | | |
|---|---|---|
| CN | 1875996 A | 12/2006 |
| CN | 101474236 A | 7/2009 |
| CN | 102429949 A | 5/2012 |
| WO | 200247703 A2 | 6/2002 |

* cited by examiner

*Primary Examiner* — Snigdha Maewall
(74) *Attorney, Agent, or Firm* — Novick, Kim & Lee, PLLC; Allen Xue

(57) ABSTRACT

The pharmaceutical composition is a formulation prepared by the raw materials in parts by weight: 1-300 parts of chlorogenic acid and 1-50 parts of *Ganoderma lucidum* spore oil, and the preparative process for said pharmaceutical composition was provided. Chlorogenic acid can be used compatibly with *Ganoderma lucidum* spore oil, with a synergistic effect. Inclusion technique is applied in product development to improve stability of oily liquid material *Ganoderma lucidum* spore oil and solid material chlorogenic acid obtained from the extract of *Eucommia* leaves. After inclusion by the inclusion technology, the liquid drugs become powder, and thus easily oxidized natural products could be protected. Moreover, the damage for active ingredients caused by air can be prevented, and the stability and the taste may get improved.

5 Claims, No Drawings

PHARMACEUTICAL COMPOSITION, PREPARATION METHOD THEREFOR AND USE THEREOF

TECHNICAL FIELD

The present invention relates to a pharmaceutical composition and its method of preparation, particularly a composition that comprises chlorogenic acid and *Ganoderma lucidum* spore oil.

BACKGROUND OF THE INVENTION

Chlorogenic acid is a phenylpropanoid compound produced by the cinnamic acid pathway during aerobic respiration of plants. It widely exists in various plants and plays a role of antisepsis, antibiosis, antivirus in the process of plant growth, thus is awarded a good reputation of "white blood cells in plant". At home and abroad, chlorogenic acid is one of hot drugs being investigated for its anticancer, antivirus, and anti-AIDS properties.

*Eucommia ulmoides* Oliv. is one of plants with high content of chlorogenic acid, and the chlorogenic acid extracted from leaves of *E. ulmoides* has pleiotropic actions, including antibiosis, antivirus, cholaneresis, hepatoprotection, blood pressure release, excitation of central nervous system, and so on. Chlorogenic acid also has effects on digestive system, hematological system, and genital system, and possesses wide antibacterial, antiviral, antimutagenic, and antineoplastic properties. In addition, chlorogenic acid further has an ability of stimulating small bowel peristalsis, promoting biligication, cholaneresis, stopping bleeding, raising up white blood cell, shortening blood coagulation, and antioxidant activity. Experimental results have shown caffeic acid, as a hydrolysate of chlorogenic acid, also has effects of cholaneresis and raising up white blood cell; caffeic acid, possessing predominant therapeutic effects on acute infectious disease caused by bacteria, as well as leucopenia resulted from radiotherapy and chemotherapy, becomes a plant-derived monomeric medicine receiving much concerns in the world.

*Ganoderma lucidum*, as a treasure in traditional Chinese medicine, is a medicinal fungus possessing longevity- and vigor-promoting functions. *Ganoderma lucidum* spore oil is lipid materials extracted from dry spores after spore wall is broken by physical methods. Said oil, mainly containing triterpenoids, sterols, etc., is an active fraction of *Ganoderma lucidum* spores. A study on its effects has shown the oil has functions of enhancing immunity, protecting liver, antivirus, regulating blood fat, together with beneficial regulatory effects on nervous system, cardiovascular system, and respiratory system. Furthermore, *Ganoderma lucidum* spore oil can promote physiological activity of immunocytes, and restore immunobiological functions of organism. The oil is an effective agent with anticancer and immunoregulatory action, and can overall enhance the constitution of patients with tumor, thus delay or prevent the occurrence of neoplasms complications; combined with surgery and chemo-radiation, the oil can promote postoperative rehabilitation, and be used as an adjunctive therapy after radiotherapy and chemotherapy; the oil is further used for the treatment of insomnia and amnesia, body virtual fatigue, neurasthenia; the oil is also used for the adjunctive treatment and prevention of liver disease, cardiovascular disease, and hypertension.

Currently, the reports on combinations of chlorogenic acid and *Ganoderma lucidum* spore oil cannot be found.

DESCRIPTION OF THE INVENTION

The embodiment of the present invention provides a pharmaceutical composition, formed by the combination of chlorogenic acid and *Ganoderma lucidum* spore oil. Another embodiment of the present invention provides the preparative process of said pharmaceutical composition, as well as the uses thereof.

The present invention provides The pharmaceutical composition, and the composition is a formulation containing the following materials in parts by weight:

1-300 parts of chlorogenic acid, 1-50 parts of *Ganoderma lucidum* spore oil.

Further preferably, the composition is a formulation prepared from the following materials in parts by weight:

1-300 parts of chlorogenic acid, 1-50 parts of *Ganoderma lucidum* spore oil.

Further preferably, the composition is a formulation prepared from the following materials in parts by weight:

100-300 parts of chlorogenic acid, 10-50 parts of *Ganoderma lucidum* spore oil.

Further more preferably, the composition is a formulation prepared from the following materials in parts by weight:

100-200 parts of chlorogenic acid, 10-30 parts of *Ganoderma lucidum* spore oil.

Further more preferably, the composition is a formulation prepared from the following materials in parts by weight:

160 parts of chlorogenic acid, 25 parts of *Ganoderma lucidum* spore oil.

In which, *Ganoderma lucidum* spore oil used is above second grade, as a translucent oily liquid of golden yellow or brownish red. The oil has a special fragrance for *Ganoderma lucidum* spore oil. At low temperature, there is the presence of sediments or coagulation in the oil. The oil has a triterpenoid content of $\geq 15\%$, a triglyceride content of $\geq 60\%$, an iodine value of 55%, an acid value up to 15 mg KOH/g, and the water content of $\leq 2\%$. In the oil, the content of arsenic is <0.5 mg/Kg, the content of lead <1 mg/Kg, the content of mercury <0.1 mg/Kg, and the content of cadmium (Cd) $\leq 0.5$ mg/kg. In addition, the total bacterial count is <1000/g, the total mould number <50/g, the coliform bacteria <30, and pathogenic bacteria cannot be detected.

The pharmaceutical composition according to the present invention is a formulation prepared from active ingredients chlorogenic acid and *Ganoderma lucidum* spore oil, together with pharmaceutically acceptable excipients or auxiliary constituents.

Said formulations are buccal or oral preparations; preferably, said buccal preparations are buccal tablet, mucoadhesive tablet, and gargle; said oral preparations are tablet, effervescent tablet, capsule, oral liquid, and pulvis.

In which, said buccal tablet is prepared from the following raw materials and adjuvants in parts by weight:

1-300 parts of chlorogenic acid, 1-50 parts of *Ganoderma lucidum* spore oil, 1-850 parts of excipients, 1-10 parts of flavoring agent, 1-70 parts of disintegrating agent, 1-50 parts of binding agent, and 1-5 parts of lubricant.

In which, said filling agents are selected from the group consisting of lactose, glucose, sorbitol, mannitol, maltitol, xylitol, and at least two species thereof; said flavoring agents are selected from the group consisting of sucrose, Aspartame, stevia, fructose, vitamin c, proteoglycan, orange flavoring agent and mixtures thereof; said diluent agents are selected from the group consisting of starch, microcrystalline cellulose, mannitol, and at least two species thereof; said disintegrating agent are selected from the group consisting of sodium hydroxymethyl starch, crospolyvinyl pyrrolidone, low-substituted hydroxypropyl cellulose, microcrystalline cellulose, pregelatinized starch and at least two species thereof; said lubricants are selected from the group consisting of magnesium stearate, calcium stearate, stearic acid, talc powder.

Further preferably, said buccal tablets is prepared from the following raw materials and adjuvants in parts by weight:

160 parts of chlorogenic acid, 140 parts of β-cyclodextrin inclusion compound of *Ganoderma lucidum* spore oil, 390 parts of mannitol, 365 parts of lactose, 100 parts of pregelatinized starch, 70 parts of hydroxypropyl cellulose, 5 parts of orange flavoring agent, 3 parts of Aspartame, 45 parts of Povidone K30, and 3 parts of magnesium stearate.

In which, said orange flavoring agent is bitter masking agent, with a model number 98AF1415. The manufacturer is Sen Xin Flavor Pigment Technology (China) Co., Ltd., and the agency is Guangzhou Tianrun Pharmaceutical Co. Ltd.

The present invention further provides a preparative process of said pharmaceutical composition, in which, said buccal tablets are prepared according to the following steps:

a. Raw materials and adjuvants are accurately weighed;

b. The inclusion compound of *Ganoderma lucidum* spore oil are formed using β-cyclodextrin;

c. Mixing, preparing soft materials, granulating, drying, breaking, tableting, thus obtaining tablets.

The present invention further provides the use of said pharmaceutical composition in preparation of medicaments or health care products that can improve the non-specific immunity function and the scavenging ability of oxygen radicals of organisms.

For the raw drug materials of the present invention, chlorogenic acid can be used compatibly with *Ganoderma lucidum* spore oil, with a synergistic effect. In study on the combination of chlorogenic acid and *Ganoderma lucidum* spore oil, characteristics of raw materials are fully considered, and inclusion technique is applied in product development, to realize the stable coexistence of oily liquid material *Ganoderma lucidum* spore oil and solid material chlorogenic acid obtained from the extract of *Eucommia* leaves. After inclusion by the inclusion technology, the liquid drugs become powder, and thus easily oxidized natural products could be protected. Moreover, the damage for active ingredients caused by air can be prevented, and the stability and the taste may get improved, that provide a new choice for clinical use.

EXAMPLES

Example 1 Screening Test of Adjuvant Materials Used in Buccal Tablets of Medicament According to the Present Invention The raw materials contain more extracts, and its fluidity is bad, thus tableting is needed following granulating. Based on these characteristics, screening of adjuvant materials is carried out.

Mannitol does not absorb moisture, and its dissolution is accompanied by heat absorption, leading to a comfortable feeling in oral cavity, thus, it is most commonly used in chewable tablets; considering following reasons, i.e. the absence of hygroscopicity, its stable nature, not having chemical reactions with most medicaments, as well as obtaining bright, clean, and beautiful tablets, lactose can be used to improve the smooth surface of tablets. Using mannitol and lactose as filling agents, together with water, 70% ethanol, and 90% ethanol as binders, respectively, all of them were mixed with raw materials at predetermined amount for each tablet, and screening of binders was carried out.

Formulations for preliminary test of screening out adjuvant materials are as follows:

| | |
|---|---|
| Chlorogenic acid | 250 g |
| *Ganoderma lucidum* spore oil | 50 g |
| Mannitol | 350 g |
| Lactose | 350 g | sum 1000 g, preparing 1000 tablets, 1 g/tablet.

As for wet granulation, referring to the amounts used in literature, screening of binders was carried out, and results were depicted in Table 1:

TABLE 1

| Screening test of binders | |
|---|---|
| Binder | Description of materials |
| Water | Poor viscidity, not easy to granulation |
| 95% ethanol | Poor viscidity, not easy to granulation |
| 5% starch slurry | Strong viscidity, easy to form lump of materials |
| Carboxymethyl cellulose sodium | Strong viscidity, easy to form lump of materials |
| 5% PVP90% ethanol | better viscidity and dispersibility |

Since *Ganoderma lucidum* spore oil was liquid, without pretreatment, direct application cannot be easily well-mixed. By assay, the content uniformity of *Ganoderma lucidum* triterpenoids was poor, and if exposed in circumstances and contacting with air for a long time, it can be easily oxidized, and produce a bad rancid flavour. Thus, the preprocessing of forming inclusion complexes with β-cyclodextrin was necessary for feeding.

Considering the unstable structure of chlorogenic acid containing polyphenols and an ester, together with preliminary results of pretesting, PVP90% EtOH was chosen as binder.

The present invention was intended to prepare tablets for oral use, with higher hardness, so as to decrease the friability and ensure the integrity of products during transportation and storage. Considering that the target population may take the product by buccal way, a small amount of disintegrating agent were added, to promote the solution rate of tablets while being held in mouth and chewed, and thus hydroxypropyl cellulose, with better taste and compressibility, was chosen. Hydroxypropyl cellulose, with good inertness, was compatible with various medicaments, and can be used in solid preparations as binder and disintegrating agent. Especially, it was suitable for "internal addition", and may obviously improve the hardness of tablet, accelerate its disintegration and release.

In the formulation, the remedium cardinale was pure chlorogenic acid extracted from Folium Eucommiae, and its taste was acerbity-astringent, thus a suitable amount of Aspartame and orange flavoring agent was added for masking; magnesium stearate, commonly used in chewable tablets, was added as lubricants, and can improve fluidity of granules and prevent occurrence of sticking.

Investigation on Inclusion Process of *Ganoderma Lucidum* Spore Oil:

The inclusion compound was prepared by saturated water solution method. *Ganoderma lucidum* spore oil was accurately weighed, added to 95% EtOH, homogenized, and dissolved by warming, to which saturated water solution of β-cyclodextrin at a temperature of 60~70° C. was added, then stirred for more than 1 h. Then, heating was stopped, but stirring was continued for further 3 h, to obtain white precipitate. After kept at room temperature for 12 h, the precipitate was filtered and washed with absolute alcohol for three times, until the oil on the surface disappeared. The precipitate was dried at 60° C., and sifted with a 60 mesh sieve.

$$\text{Inclusion rate \%} = \frac{\text{Actual oil content in inclusion complexes}}{\text{oil feeding amount}} \times 100$$

$$= \frac{\text{Total triterpenoid content in inclusion complexes}}{\text{Total triterpenoid content in oil}} \times 100$$

$$\text{Yield of inclusion complexes \%} = \frac{\text{Actual amount of inclusion complexes}}{\text{Total amount of } \beta\text{-cyclodextrin + oil feeding}} \times 100$$

$L_9(3^4)$ orthogonal experiments were performed by selecting four major factors and three indexes, said major factors included the feed ratio of *Ganoderma lucidum* spore oil and β-cyclodextrin, the feed ratio of β-cyclodextrin and water, the inclusion temperature, and the stirring time, while said three indexes included the yield of volatile oil, the utilization rate, and the inclusion rate. Level of factors was depicted in Table 2.

According to the design, nine groups of experiment were carried out, and results were shown in Table 3. The order of factor effects on inclusion process was D>A>C>B, and as visual analysis, the best combination was A2B2C3D1. By range comparison, for C2 and C3, k values of the inclusion rate and the yield of inclusion complexes seemed to be minor different, indicating the inclusion times 3 h and 6 h have little effects on the inclusion result. Combined with the consideration of time factor, C2 level was thus chosen. The conditions were determined as A2B2C2D1, i.e. *Ganoderma lucidum* spore oil: β-cyclodextrin (g:g)=1:6, temperature/° C.=60, time/h=3, β-cyclodextrin:water/g:ml=1:4.

Validation of Inclusion Process

As the definitive optimization conditions, three batches of products were used for the validation of inclusion process.

0.5 kg of *Ganoderma lucidum* spore oil was measured out, and added into 3 L of 95% EtOH, then stirred to obtain an uniform mixture. The mixture was warmed to dissolve the oil, then the solution of β-cyclodextrin (3 kg) in 12 L water at 60~70° C. was slowly added, and stirred for 3 h. Heating was ceased, but stirring was continued for further 3 hours, to obtain the white precipitation. After kept at room temperature for 12 h, the precipitate was filtered and washed with absolute alcohol for three times, until the oil on the surface disappeared. The precipitate was dried at 60° C., and sifted with a 60 mesh sieve.

TABLE 2

Level of factors

| Level | A *Ganoderma lucidum* spore oil:β-cyclodextrin g:g | B Inclusion temperature/° C. | C Inclusion time/h | D β-cyclodextrin:water/ g:ml |
|---|---|---|---|---|
| 1 | 1:4 | 80 | 1 | 1:4 |
| 2 | 1:6 | 60 | 3 | 1:7 |
| 3 | 1:8 | 40 | 6 | 1:10 |

TABLE 3

Orthogonal experimental results of inclusion complexes formed between *Ganoderma lucidum* spore oil and β-cyclodextrin

| | | No. | A | B | C | D | Inclusion rate (%) | Yield of inclusion complexes (%) |
|---|---|---|---|---|---|---|---|---|
| | | 1 | 1 | 1 | 1 | 1 | 73.50 | 88.62 |
| | | 2 | 1 | 2 | 2 | 2 | 77.28 | 90.26 |
| | | 3 | 1 | 3 | 3 | 3 | 69.94 | 87.53 |
| | | 4 | 2 | 1 | 2 | 3 | 77.70 | 89.36 |
| | | 5 | 2 | 2 | 3 | 1 | 92.24 | 92.87 |
| | | 6 | 2 | 3 | 1 | 2 | 75.60 | 89.54 |
| | | 7 | 3 | 1 | 3 | 2 | 84.18 | 91.21 |
| | | 8 | 3 | 2 | 1 | 3 | 75.70 | 88.51 |
| | | 9 | 3 | 3 | 2 | 1 | 85.08 | 89.85 |
| Inclusion rate | k1 | 73.573 | 78.460 | 74.933 | 83.607 | | | |
| | k2 | 81.847 | 81.740 | 80.020 | 79.020 | | | |
| | k3 | 81.653 | 76.873 | 82.120 | 74.447 | | | |
| | R | 8.273 | 4.867 | 7.187 | 9.160 | | | |
| Yield of inclusion complexes | k1 | 88.803 | 89.730 | 88.890 | 90.447 | | | |
| | k2 | 90.590 | 90.547 | 89.823 | 90.337 | | | |
| | k3 | 89.857 | 88.973 | 90.537 | 88.467 | | | |
| | R | 1.787 | 1.573 | 1.647 | 1.980 | | | |

TABLE 4

Validation of three batches of products

| No. | Yield of inclusion complexes (%) | Inclusion rate (%) | Odor of inclusion complexes |
|---|---|---|---|
| 1 | 94.22 | 91.55 | Pure odor, without tapinoma-odor of oils |
| 2 | 94.57 | 90.48 | Pure odor, without tapinoma-odor of oils |
| 3 | 95.14 | 91.06 | Pure odor, without tapinoma-odor of oils |

According to the validation results in Table 4, the process had a good stability, and was applied to the inclusion of *Ganoderma lucidum* spore oil.

Formulation Screening and Technical Study of Tablets

Since chlorogenic acid was more sensitive to light, heat, and moisture, mannitol can improve the stability and be used in the formulation. In addition, the reducing sugar lactose was used as excipient, the solution of Povidone K30 in EtOH as binder, hydroxypropyl cellulose as disintegrating agent, to realize the effect of shortening granulation time, reducing granulation temperature, lowering drying temperature, together with a short dry time and a rapid disintegration for tablets.

Raw materials and adjuvant materials were measured out, sifted with a 60 mesh sieve, and uniformly mixed. The solution of Povidone K30 in 85% EtOH (10%) was added, to prepare soft materials, that was used to preparing particles using 20 mesh sieve and then dried at 60° C. The water content was detected using appearance, taste, and hardness as examination indicators. Results were shown in Table 5.

TABLE 5

Four formulations designed for screening out filling agent

| Raw/adjuvant materials | Formulation 1 | Formulation 2 | Formulation 3 | Formulation 4 |
|---|---|---|---|---|
| Chlorogenic acid (g) | 200 | 200 | 200 | 200 |
| Inclusion complexes *Ganoderma lucidum* spore oil | 30 | 30 | 30 | 30 |
| β-cyclodextrin | 180 | 180 | 180 | 180 |
| Mannitol (g) | 500 | 250 | 200 | 250 |
| Lactose (g) | — | 250 | 250 | 200 |
| Pregelatinized starch (g) | — | — | 50 | 50 |
| Hydroxypropyl cellulose (g) | 50 | 50 | 50 | 50 |
| Orange flavoring agent (g) | 4 | 4 | 4 | 4 |
| Aspartame (g) | 3 | 3 | 3 | 3 |
| Povidone K30 (g) | 35 | 35 | 35 | 35 |
| Magnesium stearate (g) | 3 | 3 | 3 | 3 |
| Appearance | Coarse | Smooth and intact | Smooth and intact | Smooth and intact |
| Tablet weight variation (RSD %) | 5.68 | 6.83 | 6.34 | 5.18 |
| Taste | Very sweet | Sweeter | Gritty sense | Sweet and tasty |
| Hardness | 110N | 80N | 65N | 75N |

According to the results, formulation 1 just used mannitol as excipient, and the obtained materials jammed punch, producing tablets with coarse surface and larger hardness. Based on formulation 1, formulation 2 used mannitol-lactose (1:1) as excipient, and obtained tablets with smooth and intact appearance, suitable hardness, and sweeter taste. Based on formulation 2, formulation 3 was made a slight adjustment, and the usage amount of mannitol was reduced, accompanied by addition of a small amount of pregelatinized starch, to obtain tablets with better appearance. But due to the reduced hardness, the tablets tasted gritty. Based on formulation 3, in formulation 4, the ratio of lactose and mannitol was adjusted, to obtain tablets with good appearance and taste, as well as suitable hardness. During granulation process, above four formulations produced tablets with a great tablet weight variation, that should be correlated with the addition amount of chlorogenic acid possessing poorer fluidity and compressibility, and thus its addition amount need make a suitable adjustment.

Based on formulation 4 for preliminary screening, the ratio of raw materials and excipients, the ratio of lactose and mannitol in excipient, and the concentration of binder was further optimized. The level of factors was shown in Table 6.

TABLE 6

Factor-level Table

| | Factors | | | |
|---|---|---|---|---|
| level | A Chlorogenic acid:inclusion complexes (g:g) | B Raw materials:excipient (g:g) | C Mannitol:lactose (g:g) | D Concentration of binder (B) |
| 1 | 150:150 | 300:600 | 300:300 | 4% |
| 2 | 160:140 | 300:700 | 300:280 | 7% |
| 3 | 180:120 | 300:850 | 300:220 | 10% |

According to above orthogonal factor-level table 6, the usage amount of raw and adjuvant materials for each experiment was determined, and then they were mixed. To the mixture, was added the corresponding concentration of binder, to prepare soft materials. Using "Light pinch into a group, light pressure that is broken" as decision method of soft materials, the usage volume of binder was recorded; the soft materials was dried in air blowing oven at 60° C., until the moisture content was 3%, and then breaking was performed by passing through No. 2 sieve, to obtain granules after dry. 0.3% lubricant was incorporated, followed by tableting.

After dry, the repose angle of granules, the yield of granules, and the appearance and the hardness of tablets were used as evaluation indicators, and each factor-level experiment was scored. Once scores of four indicators were added together, the total score of each factor-level experiment was gotten and evaluated, to inspect effects of each factor on tablet molding. The results of orthogonal experiment were shown in Table 7.

TABLE 7

The results of orthogonal experiment using SPSS design

| No. | A | B | C | D | Total score |
|---|---|---|---|---|---|
| 1 | 3 | 2 | 3 | 1 | 5.89 |
| 2 | 3 | 3 | 1 | 2 | 10.22 |
| 3 | 2 | 1 | 3 | 2 | 12.87 |
| 4 | 2 | 3 | 2 | 1 | 18.88 |
| 5 | 2 | 2 | 1 | 3 | 14.94 |
| 6 | 1 | 3 | 3 | 3 | 13.89 |

TABLE 7-continued

The results of orthogonal experiment using SPSS design

| No. | A | B | C | D | Total score |
|---|---|---|---|---|---|
| 7 | 1 | 1 | 1 | 1 | 8.20 |
| 8 | 3 | 1 | 2 | 3 | 14.65 |
| 9 | 1 | 2 | 2 | 2 | 12.70 |
| 10 | 3 | 2 | 3 | 1 | 8.64 |
| 11 | 3 | 3 | 1 | 2 | 14.37 |
| 12 | 2 | 1 | 3 | 2 | 14.39 |
| 13 | 2 | 3 | 2 | 1 | 16.31 |
| 14 | 2 | 2 | 1 | 3 | 16.42 |
| 15 | 1 | 3 | 3 | 3 | 16.0 |
| 16 | 1 | 1 | 1 | 1 | 9.0 |
| 17 | 3 | 1 | 2 | 3 | 14.75 |
| 18 | 1 | 2 | 2 | 2 | 9.62 |

Statistical analysis was carried out using SPSS software, and results are shown in the following table.

TABLE 8

Experimental results of orthogonal statistical analysis

| Source | III type Sum of square | df | Mean square | F | Sig. |
|---|---|---|---|---|---|
| Calibration model | 185.643 | 9 | 20.627 | 7.396 | .005 |
| Intercept | 2983.524 | 1 | 2983.524 | 1069.776 | .000 |
| Chlorogenic acid:inclusion complexes (A) | 68.652 | 2 | 34.326 | 12.308 | .004 |
| Raw material:excipient (B) | 41.245 | 2 | 20.623 | 7.394 | .015 |
| Mannitol:lactose(C) | 23.525 | 2 | 11.763 | 4.218 | .056 |
| Concentration of binder (D) | 49.293 | 2 | 24.646 | 8.837 | .009 |
| Repeated experiment | 2.928 | 1 | 2.928 | 1.050 | .336 |
| Error | 22.311 | 8 | 2.789 | | |
| Total | 3191.478 | 18 | | | |
| Corrected total | 207.954 | 17 | | | | a. $R^2$ = 0.893 (adjusted $R^2$ = 0.772)

Results indicated the ratio of chlorogenic acid and inclusion complexes (A), as well as the concentration of binder (D) showed very significant difference, and were the main influential factors influencing the tablet molding; various ratios of raw materials and excipients (B) showed significant difference, and the ratio (B) was the secondary factor influencing the tablet molding.

According to the results of Tables 9 and 10, the ratio 160:140 of chlorogenic acid and inclusion complexes excelled two additional ratios; 10% concentration of binder excelled two additional concentrations of binder.

TABLE 9

The mean estimation table for ratios of chlorogenic acid and inclusion complexes

| Ratio of chlorogenic acid and inclusion complexes | Mean | Standard error | 95% confidence intervals | |
|---|---|---|---|---|
| | | | Lower limit | Upper limit |
| 150:150 | 11.568 | .682 | 9.996 | 13.141 |
| 160:140 | 15.635 | .682 | 14.063 | 17.207 |
| 180:120 | 11.420 | .682 | 9.848 | 12.992 |

TABLE 10

The mean estimation table for the concentrations of binder

| Concentration of binder | Mean | Standard error | 95% confidence intervals | |
|---|---|---|---|---|
| | | | Lower limit | Upper limit |
| 4% | 11.153 | .682 | 9.581 | 12.726 |
| 7% | 12.362 | .682 | 10.789 | 13.934 |
| 10% | 15.108 | .682 | 13.536 | 16.681 |

For the mean estimation of the ratio of raw materials and excipient, results showed the ratio 300:850 of raw materials and excipient excelled two additional ratios.

TABLE 11

The mean estimation table for ratios of raw materials and excipient

| Ratio of raw materials and excipient | Mean | Standard error | 95% confidence intervals | |
|---|---|---|---|---|
| | | | Lower limit | Upper limit |
| 300:600 | 12.310 | .682 | 10.738 | 13.882 |
| 300:700 | 11.368 | .682 | 9.796 | 12.941 |
| 300:850 | 14.945 | .682 | 13.373 | 16.517 |

For the mean estimation of the ratio of mannitol and lactose, results showed the ratio 300:280 of mannitol and lactose excelled two additional ratios. Results are shown in the following table.

TABLE 12

The mean estimation for ratios of mannitol and lactose

| Ratio of mannitol and lactose | Mean | Standard error | 95% confidence intervals | |
|---|---|---|---|---|
| | | | Lower limit | Upper limit |
| 300:300 | 12.192 | .682 | 10.619 | 13.764 |
| 300:280 | 14.485 | .682 | 12.913 | 16.057 |
| 300:220 | 11.947 | .682 | 10.374 | 13.519 |

Consequently, by variance analysis for effects of each factor on tablet molding, the ratio 160:140 of chlorogenic acid and inclusion complexes, 10% concentration of binder, the ratio 300:850 of raw materials and excipient, and the ratio 300:280 of mannitol and lactose were the optimal selection.

Results of orthogonal experiment were combined, and the final formulation was determined as follows:

| | |
|---|---|
| Chlorogenic acid | 160 g |
| Inclusion complexes formed between Ganoderma lucidum spore oil and β-cyclodextrin | 140 g |
| mannitol | 390 g |
| lactose | 365 g |
| pregelatinized starch | 100 g |
| hydroxypropyl cellulose | 70 g |
| orange flavoring agent | 5 g |
| Aspartame | 3 g |
| Magnesium stearate | 3 g |
| Povidone K30 | 45 g |

Total 1000 tablets were prepared by granulating and tableting.

Investigation on Stability

As the optimal formulation, materials were taken out, and *Ganoderma lucidum* spore oil formed inclusion complexes with β-cyclodextrin, while other solid materials passed through 60 mesh sieve. After raw materials and adjuvant materials were uniformly mixed, the solution of Povidone K30 in 85% EtOH (10%) was added, to prepare soft materials. Then, the soft materials passed through a 20 mesh sieve by means of forced extrusion, to prepare granules, and the resulted wet granules were dried at 60° C. for 3 h. The dry particles passed through 20 mesh sieve for breaking, to which magnesium stearate was added, followed by tableting.

Three patches of samples prepared were placed in constant temperature and humidity cabinet at temperature of 38° C.±1° C. under relative humidity of 75% for the accelerated stability test, and results were shown in Table 13.

TABLE 13

Results of accelerated stability test

| | Batch | | | | | | | | | | | |
|---|---|---|---|---|---|---|---|---|---|---|---|---|
| | 1 | | | | 2 | | | | 3 | | | |
| Items | 0 month | 1 month | 2 monthes | 3 monthes | 0 month | 1 month | 2 month | 3 month | 0 month | 1 month | 2 month | 3 month |
| Chlorogenic acid #/(g/100 g) | 12.7 | 12.2 | 12.5 | 12.4 | 12.4 | 12.5 | 12.0 | 20.1 | 12.3 | 12.2 | 12.4 | 12.1 |
| Total triterpenoids (taking oleanolic acid account)/(mg/100 g) | 353 | 350 | 330 | 326 | 321 | 318 | 315 | 313 | 320 | 322 | 318 | 321 |

Experiment confirmed the buccal tablets of chlorogenic acid produced by said process had stable quality, and the process was reasonable.

In the hereinafter, detailed pharmacodynamics experiments were used to prove the beneficial effects of the present invention.

Example 1 Comparison of Effects on Immunologic Functions of Chlorogenic Acid—*Ganoderma Lucidum* Spore Oil Combination According to the Pharmaceutical Composition of the Present Invention with their Single Use Experimental Grouping and Dose Design

TABLE 14

Experimental grouping and dose design table

| Group | Name | Dose (mg/kg) | Concentration (mg/ml) |
|---|---|---|---|
| Single-use group 1 | Chologenic acid | 300 | 15 |
| Single-use group 2 | *Ganoderma lucidum* spore oil | 300 | 15 |
| Combination 1 | Chlorogenic acid-*Ganoderma lucidum* spore oil (100:10) | 300 | 15 |
| Combination 2 | Chlorogenic acid-*Ganoderma lucidum* spore oil (200:30) | 300 | 15 |
| Combination 3 | Chlorogenic acid-*Ganoderma lucidum* spore oil (300:50) | 300 | 15 |
| Negative control group | Physiological saline | — | — |
| Positive control group | Mannatide | 20 | 1 |

1) Phagocytosis Test of Chicken Red Blood Cell

Kunming mice were randomly divided into seven groups according to gender and body weight, with 12 mice in each group. As the dose design, all groups received one intragastric administration per day at a dose of 0.4 ml/20 g for successive four weeks. Mice were weighed for two times per week, to adjust the drug dosage. 30 minutes after final administration, each mouse in each group was injected intraperitoneally with 5% chicken erythrocyte suspension at a dose of 1.0 ml/mouse. Six hours after injection, animals were sacrificed by cervical dislocation, and received 2 ml physiological saline via peritoneal injection, while the abdomen of mice was gently massaged. Then, one pin hole was cut in the center of peritoneum, and washing water in peritoneal cavity was extracted, dropped on microscope slide, and cultured for 30 min in incubator at 37° C. The solution was washed with normal saline, fixed using methanol, and dyed by Giemsa staining. The numbers of chicken red blood cell phagocytized by 100 macrophages were observed under oil immersion lens. The phagotrophic percentage and the phagotrophic index were calculated according to the following formula, and results were shown in Table 15.

$$\text{The phagotrophic percentage \%} = \frac{\text{The macrophage numbers phagocytizing chicken red blood cells}}{100 \text{ macrophages}} \times 100$$

$$\text{The phagotrophic index \%} = \frac{\text{The total of red blood cells phagocytized by macrophages}}{100 \text{ macrophages}} \times 100$$

TABLE 15

Phagotrophic experimental results of chicken red blood cells

| Group | Name | Phagotrophic percentage (%, $\overline{X} \pm SD$) | Phagotrophic index ($\overline{X} \pm SD$) |
|---|---|---|---|
| Single-use group 1 | Chologenic acid | 36.58 ± 4.50** | 0.52 ± 0.07** |
| Single-use group 2 | Ganoderma lucidum spore oil | 35.87 ± 3.27** | 0.49 ± 0.04** |
| Combination 1 | Chlorogenic acid-Ganoderma lucidum spore oil (100:10) | 38.68 ± 3.56*Δ | 0.56 ± 0.03*Δ |
| Combination 2 | Chlorogenic acid-Ganoderma lucidum spore oil (200:30) | 38.25 ± 3.47*Δ | 0.56 ± 0.04*Δ |
| Combination 3 | Chlorogenic acid-Ganoderma lucidum spore oil (300:50) | 38.05 ± 4.22*Δ | 0.55 ± 0.06*Δ |
| Negative control group | Physiological saline | 31.56 ± 2.62 | 0.44 ± 0.04 |
| Positive control group | Mannatide | 40.32 ± 2.25*ΔΔ | 0.57 ± 0.05*ΔΔ |

Compared with the negative group,
**P < 0.01
***P < 0.001;
compared with the single-use group,
ΔP < 0.05,
ΔΔP < 0.01.

Results indicated comparison of the single-use group with the negative group showed very significant difference (P<0.01); comparison of the combination group with the negative group showed very significant difference (P<0.01), while comparison of the combination group with the single-use group showed significant difference (P<0.05).

2) Carbon Granules Clearance Test

Kunming mice were randomly divided into seven groups according to gender and body weight, with 10 mice in each group. As the dose design in Table 14, all groups were administrated once per day at a dose of 0.4 ml/20 g for successive four weeks. Mice were weighed for two times per week, to adjust the drug dosage. One hour after final administration, each mouse in each group was injected with Indian ink [(1:4)0.1 ml·10 g$^{-1}$] via vena caudalis. One minute and five minutes after injection, 20 μl blood samples were drawn from orbit, respectively, added to the solution containing 4 ml 0.1% $Na_2CO_3$, and scanned under a wavelength range of 400 nm-700 nm, then a colorimetric assay was performed at the maximum absorption wavelength of 576 nm. After animals were sacrificed by cervical dislocation, liver and spleen were collected and weighed, to calculate the phagotrophic index $K=(\log OD^1-\log OD_2)/(t_2-t_1)$ and correct the phagotrophic index $\alpha=[body\ weight/(liver\ weight+spleen\ weight)]\times K^{1/3}$. Experimental results were shown in Table 16.

TABLE 16

Experimental results of carbon granules clearance

| Group | Name | K value ($\overline{X} \pm SD$) | α value ($\overline{X} \pm SD$) |
|---|---|---|---|
| Single-use group 1 | Chologenic acid | 0.019 ± 0.011 | 3.94 ± 1.05 |
| Single-use group 2 | Ganoderma lucidum spore oil | 0.018 ± 0.013 | 3.57 ± 1.28 |
| Combination 1 | Chlorogenic acid-Ganoderma lucidum spore oil (100:10) | 0.024 ± 0.012* | 4.37 ± 0.91** |
| Combination 2 | Chlorogenic acid-Ganoderma lucidum spore oil (200:30) | 0.026 ± 0.017* | 4.14 ± 1.17** |
| Combination 3 | Chlorogenic acid-Ganoderma lucidum spore oil (300:50) | 0.026 ± 0.014* | 4.26 ± 0.92** |
| Negative control group | Physiological saline | 0.008 ± 0.007 | 2.51 ± 1.45 |
| Positive control group | Mannatide | 0.019 ± 0.013 | 4.43 ± 1.06** |

Compared with the negative control group,
*P < 0.05,
**P < 0.01

Results indicated by comparison of the combination group with the negative group, K values showed significant difference P<0.05, and α values showed very significant difference (P<0.01); comparison of the single-use group with the negative group did not show significant difference.

According to the results in Tables 15 and 16, for the phagocytosis test of chicken red blood cells, the single-use group and the combination group both can very significantly increase the phagotrophic percentage and the phagotrophic index that the mouse peritoneal macrophages phagocytized chicken red blood cells; for carbon granules clearance test, the combination group can obviously increase the phagotrophic index K and the corrected phagotrophic index α of mouse macrophages. Experimental results indicated chlorogenic acid and Ganoderma lucidum spore oil, especially their combinations, can improve the phagotrophic functions of macrophages and non-specific immunologic functions of mice.

2. Effects of Combinations and Single Use on Metabolism of In Vivo Oxygen Radicals Experimental Group and Dose Design

TABLE 17

Experimental group and dose design table

| Group | Name | Dose (mg/kg) | Concentration (mg/ml) |
|---|---|---|---|
| Single-use group 1 | Chologenic acid | 300 | 15 |
| Single-use group 2 | Ganoderma lucidum spore oil | 300 | 15 |
| Combination 1 | Chlorogenic acid-Ganoderma lucidum spore oil (100:10) | 300 | 15 |
| Combination 2 | Chlorogenic acid-Ganoderma lucidum spore oil (200:30) | 300 | 15 |
| Combination 3 | Chlorogenic acid-Ganoderma lucidum spore oil (300:50) | 300 | 15 |
| Negative control group | Physiological saline | — | — |
| Positive control group | IFNa-2b | 300 0000 IU | 15 0000 IU |

Experimental methods: $C_{57}BL/6$ mice were randomly divided to eight groups as body weight, with 10 mice in each group. According to the dose design in Table 14, all groups received one intragastric administration per day at a dose of 0.4 ml/20 g for successive four weeks. Mice were weighed for two times per week, to adjust the drug dosage. On the last day of experiment, blood samples were drawn from femoral artery of animals and centrifuged to collect blood serum. Using TBA colorimetric method and xanthine oxidase method, application of sample was performed according to procedures of kit instructions, and absorbance values were measured at wavelengths of 532 nm and 550 nm using UV2300 Ultraviolet spectrophotometer. MDA content and SOD activity were calculated, respectively.

Experimental results were shown in Table 18.

TABLE 18

Experimental results of oxygen radicals metabolism ($\bar{x} \pm s$)

| Group | Name | SOD(U/L) ($\bar{x} \pm s$) | MDA(nmol/L) ($\bar{x} \pm s$) |
|---|---|---|---|
| Single-use group 1 | Chologenic acid | 218.73 ± 25.32* | 27.14 ± 3.41 |
| Single-use group 2 | Ganoderma lucidum spore oil | 213.32 ± 31.43* | 28.45 ± 7.97 |
| Combination 1 | Chlorogenic acid-Ganoderma lucidum spore oil (100:10) | 253.48 ± 26.90***Δ | 25.63 ± 2.02* |
| Combination 2 | Chlorogenic acid-Ganoderma lucidum spore oil (200:30) | 252.71 ± 31.61***Δ | 25.11 ± 4.42* |
| Combination 3 | Chlorogenic acid-Ganoderma lucidum spore oil (300:50) | 249.26 ± 13.81***Δ | 24.86 ± 9.66* |
| Negative control group | Physiological saline | 188.78 ± 11.64 | 34.29 ± 6.87 |
| Positive control group | IFNa-2b | 220.36 ± 30.56* | 28.25 ± 8.92 |

Compared with the negative group,
**$P < 0.05$
***$P < 0.001$;
compared with the blank group,
$\Delta p < 0.001$;

Results indicated: 1. when the single-use group was compared with the negative group, SOD activity significantly increased, showing statistical difference ($P<0.05$); when the combination group was compared with the negative group, SOD activity significantly increased, showing statistical difference ($P<0.001$), thus the combination group can improve oxyradical scavenging capability of organism; when the interferon group was compared with the model group, SOD activity increased to a certain extent, showing statistical difference ($P<0.05$); however, the action was weaker than the combination group, while was equal to the single-use group. 2. when the combination group was compared with the negative group, MDA content in serum significantly decreased, showing statistical difference ($P<0.05$), that suggested by improving the activity of oxyradical metabolic enzymes such as SOD and so on, the combination group can scavenge oxygen radicals, suppress lipid peroxidation reaction, and lower the MDA content in serum of mice.

Above experiments proved the combination group had an ability of improving non-specific immunologic functions of organism, as well as oxyradical scavenging capability of organism, excelled the single-use group, and the ratios 100~200:10~30 of chlorogenic acid and Ganoderma lucidum spore oil were optimal.

INDUSTRIAL APPLICATION

The compositions of the present invention had a good protective effect on oxidizable natural products, and can prevent the damage of active ingredients caused by air and improve their stability. Meanwhile, the compositions may ameliorate the taste, and possessed a rather good prospects in clinical application and industrialization.

The invention claimed is:
1. A pharmaceutical composition, comprising:
active ingredients and a pharmaceutically acceptable excipient or an auxiliary constituent, wherein: the active ingredients consist of chlorogenic acid and Ganoderma lucidum spores oil, the chlorogenic acid and Ganoderma lucidum spores oil having a weight ratio of 10:1 to 6:1; the pharmaceutically acceptable excipient comprises a filling agent and a diluent agent;
the filling agent is selected from the group consisting of lactose, glucose, sorbitol, mannitol, maltitol, xylitol, and a mixture thereof;
the diluent agent is selected from the group consisting of starch, microcrystalline cellulose, mannitol, and a mixture thereof, and
wherein said composition is a buccal preparation or an oral preparation.

2. The pharmaceutical composition according to claim 1, wherein said *Ganoderma lucidum* spore oil has a triterpenoid content of ≥15%, a triglyceride content of ≥60%, an iodine value of 55%, an acid value up to 15 mg KOH/g, a water content of ≤2%, an arsenic content of <0.5 mg/Kg, a lead content of <1 mg/Kg, a mercury content of <0.1 mg/Kg, a cadmium (Cd) content of ≤0.5 mg/kg, a total bacterial count of <1000/g, a total mould number of <50/g, and a coliform bacteria of <30/g.

3. The pharmaceutical composition according to claim 1, further comprising a pharmaceutically acceptable excipient or an auxiliary constituent.

4. The pharmaceutical composition according to claim 3, wherein said buccal preparation is a buccal tablet, a mucoadhesive tablet, or a gargle, and said oral preparation is a tablet, an effervescent tablet, a capsule, an oral liquid, or a pulvis.

5. The pharmaceutical composition according to claim 1, wherein said pharmaceutical composition is included in medicaments or health care products that improve a non-specific immunity function and a scavenging ability of oxygen radicals of organisms.

\* \* \* \* \*